United States Patent [19]

Sunamori et al.

[11] Patent Number: 5,568,267
[45] Date of Patent: Oct. 22, 1996

[54] SIMPLE TRANSMITTANCE-MEASURING INSTRUMENT

[75] Inventors: Takashi Sunamori, Funabashi; Hiroshi Sato, Narashino; Masakazu Hirose, Tokyo; Kazuo Yanauti, Funabashi, all of Japan

[73] Assignee: Taisei Chemical Industries, Ltd., Tokyo, Japan

[21] Appl. No.: 455,914

[22] Filed: May 31, 1995

[30] Foreign Application Priority Data

Feb. 17, 1995 [JP] Japan ................................ 7-029658

[51] Int. Cl.$^6$ .................................................. G01J 3/00
[52] U.S. Cl. ............................................................ 356/416
[58] Field of Search ................................... 356/402, 416; 250/226

[56] References Cited

PUBLICATIONS

"Simple Recording Film for Measurement of Integrated Global Solar Radiation" T. Yoshimura et al :Solar Energy, vol. 15, No. 5, pp. 193–204 ('89).
"Simple Measurement of Integrated Solar Radiation" T. Yoshimura et al: Int. J. Solar Energy vol. 9, pp. 193–204 ('90).
"Transistor Technique" Special No. 33, pp. 13–16 (published on May 1, 1992 by CQ Shupansha) and Translation thereof.

Primary Examiner—F. L. Evans
Attorney, Agent, or Firm—Cushman, Darby & Cushman

[57] ABSTRACT

A simple instrument for measuring the transmittance of a film impregnated with a pyridylazo-2-naphthol or dimethylphenylazo-2-naphthol dye having a continuous absorption spectrum having a plurality of absorption peaks in the wavelength range of from 350 to 800 nm, which comprises a light-emitting diode having a peak of relative emission intensity in the vicinity of a wavelength of 450 nm; a means for allowing the diode to emit a light and adjusting the quantity of the light; a band-pass filter which consists essentially of a resin film or glass plate coated with a coating composition composed essentially of at least one pigment selected from the group consisting of a Phthalocyanine Blue pigment and an organic violet pigment finely dispersed in a binder resin, and which has a peak of transmittance in the range of from 330 to 480 nm, the transmittance at the peak being 40% or more the transmittances at 260 nm or less and 520 nm or more being 1% or less, said band-pass filter being placed in such a position that the light emitted by the above light-emitting diode passes directly through the band-pass filter; a photodiode sensitive to the wavelength of the light which has passed through the band-pass filter which photodiode is placed so as to face the band-pass filter at such a space that a test sample can be inserted into between the band-pass filter and the photodiode.

7 Claims, 6 Drawing Sheets

WAVELENGTH λ (nm)
BAND-PASS FILTER BG3

SIMPLE TRANSMITTANCE-MEASURING INSTRUMENT

BACKGROUND OF THE INVENTION

This invention relates to a simple instrument for measuring the transmittance of a dye-impregnated film in such a simple, film-type integrated global solar radiation-measuring system that utilizing the fact that when the dye-impregnated film is exposed to solar radiation the dye-impregnated film is faded corresponding to the amount of the integrated solar radiation energy, the amount of the exposed integrated solar radiation energy is inferred from the degree of the color fading determined by measuring the transmittance of the film.

It is quite well-known that the amount of energy poured from the sun to the earth depends upon artificial phenomena such as an increase in the amount of carbon dioxide gas generated artificially, the destroying of the ozonesphere, the accumulation of burning products of fossil resources, and the like; and natural phenomena such as the accumulation of volcanic ash mist due to a volcanic eruption and the like, so that the natural environment surrounding human beings is changing gradually. Said change can be seized on the whole; however, the local information thereof is very little. The amount of solar radiation energy at each point in the living environment is greatly varied depending upon the configuration of the ground and the circumstances surrounding the points such as in water, in the shade of artificial structures, and the like; more specifically speaking, in the surface material of each leaf of a luxuriating plant; and the like, and it seems necessary to grasp, with an exactness to some extent, the amount of solar radiation energy in these local places and study its causual relation with various phenomena of living things, atmospheric phenomena and the like. For this purpose, a film for simply measuring the amount of solar radiation energy has already been developed which film utilizes the correlation between the degree of fading of a dye-impregnated film and the amount of the integrated solar radiation energy in the position in which the film is placed [see Yoshimura, Komiyama and Ishikawa, Solar Energy, Vol. 115, No. 5, p. 47 (1987)], and when said film is applied, it is possible to gather simultaneously data obtained in many places wherever the film may be placed. However, at present, the small pieces of the film used in the above measurements must be subjected together to measurement of absorbance by a spectrophotometer, and hence, the real situation is that the valuable benefit of simultaneous measurement at many points cannot be sufficiently utilized.

The object of this invention is to provide a simple measurement instrument aiming at simply and quickly measuring, at the measurement locales, the transmittances of simultaneous many-place-exposure samples of a dye-impregnated film having an effective exposure area of 3 cm2 or less for measuring the amount of solar radiation energy. Accordingly, the measurement instrument should have a small size and a light weight.

Moreover, as is clear from the above-mentioned object, it is necessary that the measurement precision of the instrument be such that not the mere transmittance of light but the absorbance reduced from the transmittance measured corresponds exactly to the result of measurement by a general spectrophotometer and this invention intends to obtain such a measurement instrument. If the object is to merely measure a transmittance, the measurement instrument may be relatively simple; however, in order to achieve the object of obtaining measurement values equivalent to those of a spectrophotometer by which the absorbance is determined from the transmittance measured using a sharp monochromatic light having a narrow half-value width and quantitatively determining the absorbance from them, the necessary measures must be adopted, and the main points thereof are as follows:

(1) A blue light having a wavelength of 400 to 500 nm is suitable as the monochromatic light in view of the characteristics of the absorption spectrum of the objective dye.

(2) The use of a band-pass filter is more suitable than the use of a spectral manner for taking out the monochromatic light at a low cost; however, it is difficult to obtain a band-pass filter giving a light having a narrow wavelength width and being small in reduction of quantity of light, so that it is more preferable to use a light-emitting diode (LED) which emits a monochromatic light.

(3) Though the light emitted by the light-emitting diode is a monochromatic light, its spectrum is wide, and hence, the light-emitting diode is necessarily used together with the band-pass filter. How is this problem solved, that is, how is the band-pass filter prepared for obtaining a monochromatic light having a narrower halfvalue width than the half-value width of the absorption spectrum of the objective dye for developing the necessary precision?

(4) How is a light-emitting diode which emits a blue light at a high energy obtained?

SUMMARY OF THE INVENTION

In light of the above problems, the preparation of a measurement instrument having a small size but having a precision comparable to a spectrophotometer has become necessary for the present inventors, whereby this invention has been completed.

For solving the above problem, attention has been paid to the fact that since the degree of the fading of a dye-impregnated film is measured in place of measuring the amount of solar radiation energy, the precision can be somewhat sacrificed, and it has been found that a measurement instrument having a small size and a light weight can be obtained by replacing the measurement of a transmittance using a monochromatic light by a spectral technique which is now practically used in the original spectrophotometer, by a procedure comprising adopting a high luminance-emission intensity light-emitting diode having an emission spectrum sharp to some extent as a monochromatic light source; irradiating a film with a light obtained by modifying a light emitted by the said high luminance-emission intensity light-emitting diode by passing it through a band-pass filter; allowing a photodiode to receive the light transmitted by the film; amplifying the output of the photodiode in a conventional manner: taking the quantity of the light which has passed through the film as the output voltage; and indicating this by a digital voltmeter in a conventional manner. In addition, as a result of well considering the above items (1) to (4), this invention has been completed by adopting a newly developed light-emitting diode which emits a light having a wavelength in the vicinity of 450 nm at a high luminance-emission intensity and combining this with a band-pass filter prepared by coating a resin film or glass plate with a coating composition in which a violet and/or blue pigment is so finely dispersed in a binder resin that a high transparency is shown.

According to this invention, there is provided a simple instrument for measuring the transmittance of a film impregnated with a pyridylazo-2-naphthol ($\lambda_{max}$ 468 nm) or dimethylphenylazo-2-naphthol ($\lambda_{max}$ 360, 521 nm) dye having a continuous absorption spectrum having a plurality of absorption peaks in the wavelength range of from 350 to 800 nm, which comprises a light-emitting diode having a peak of relative emission intensity in the vicinity of a wavelength of 450 nm; a means for allowing the diode to emit a light and adjusting the quantity of the light; a band-pass filter which consists essentially of a resin film or glass plate coated with a coating composition composed essentially of at lease one pigment selected from the group consisting of a Phthalocyanine Blue pigment and an organic violet pigment finely dispersed in a binder resin, and which has a peak of transmittance in the range of from 330 to 480 nm, the transmittance at the peak being 40% or more and the transmittances at 260 nm or less and 520 nm or more being 1% or less, said band-pass filter being placed in such a position that the light emitted by the above light-emitting diode passes directly through the band-pass filter; a photodiode sensitive to the light which has passed through the band-pass filter, said photodiode being placed so as to face the band-pass filter at such a space that a test sample can be inserted into between the band-pass filter and the photodiode and so as to receive the light which has passed through the band-pass filter and the test sample; and a means for transferring and digitally indicating the electrical signals from the photodiode.

BRIEF DESCRIPTION OF THE DRAWINGS

FIG. 2b is a plan view of the example of FIG. 2a.

FIG. 2c is a view showing the interior arrangement of means in the example of FIG. 2a.

FIG. 3 is the electrical circuit diagram of the example of FIG. 2a.

DETAILED DESCRIPTION OF THE INVENTION

Preferably, the simple transmittance-measuring instrument of this invention is a simple instrument for measuring the transmittance of a film impregnated with a pyridylazo-2-naphthol or dimethylphenylazo-2-naphthol dye having a continuous absorption spectrum having a plurality of peaks in the wavelength range of from 350 to 800 nm, which comprises a light source part composed mainly of a high luminance-emission intensity light-emitting diode which emits a light having a relative emission intensity peak in the vicinity of a wavelength of 450 nm and a half-value width of 70 nm or less at an emission angle of 20° or less; a means for allowing the diode to emit a light; a band-pass filter which consists essentially of a resin film or glass plate coated with a coating composition composed essentially of at least one pigment selected from the group consisting a Phthalocyanine Blue pigment and an organic violet pigment finely dispersed in a binder resin, and which has a peak of transmittance in the wavelength range of from 330 to 480 nm, the transmittance at the peak being 40% or more and the transmittances at 260 nm or less and 520 nm or more being 1% or less; and a light quantity adjuster composed of a variable resistor and an electric resistance change-over switch capable of adjusting freely the quantity of the irradiation light, and a light-receiving part composed mainly of a photodiode sensitive to the light which has passed through the band-pass filter, an amplifier and a digital voltage indicator.

The light emitted by the light-emitting diode is passed through the band-pass filter to allow the filter to partially absorb the light, thereby adjusting the light to have a half-value width narrower than the half-value width of an absorption peak of the dye-impregnated film alone, and the thus adjusted light is used as an irradiation light for measuring the transmittance of the dye-impregnated film. The quantity of the irradiation light is freely adjusted by the light quantity adjuster.

The light-emitting diode used in this invention includes specifically a high luminance-emission intensity light-emitting diode such as Light-Emitting Diode NLPB500 manufactured by Nichia Kagaku Kogyo K. K. and the like.

Figure 1:
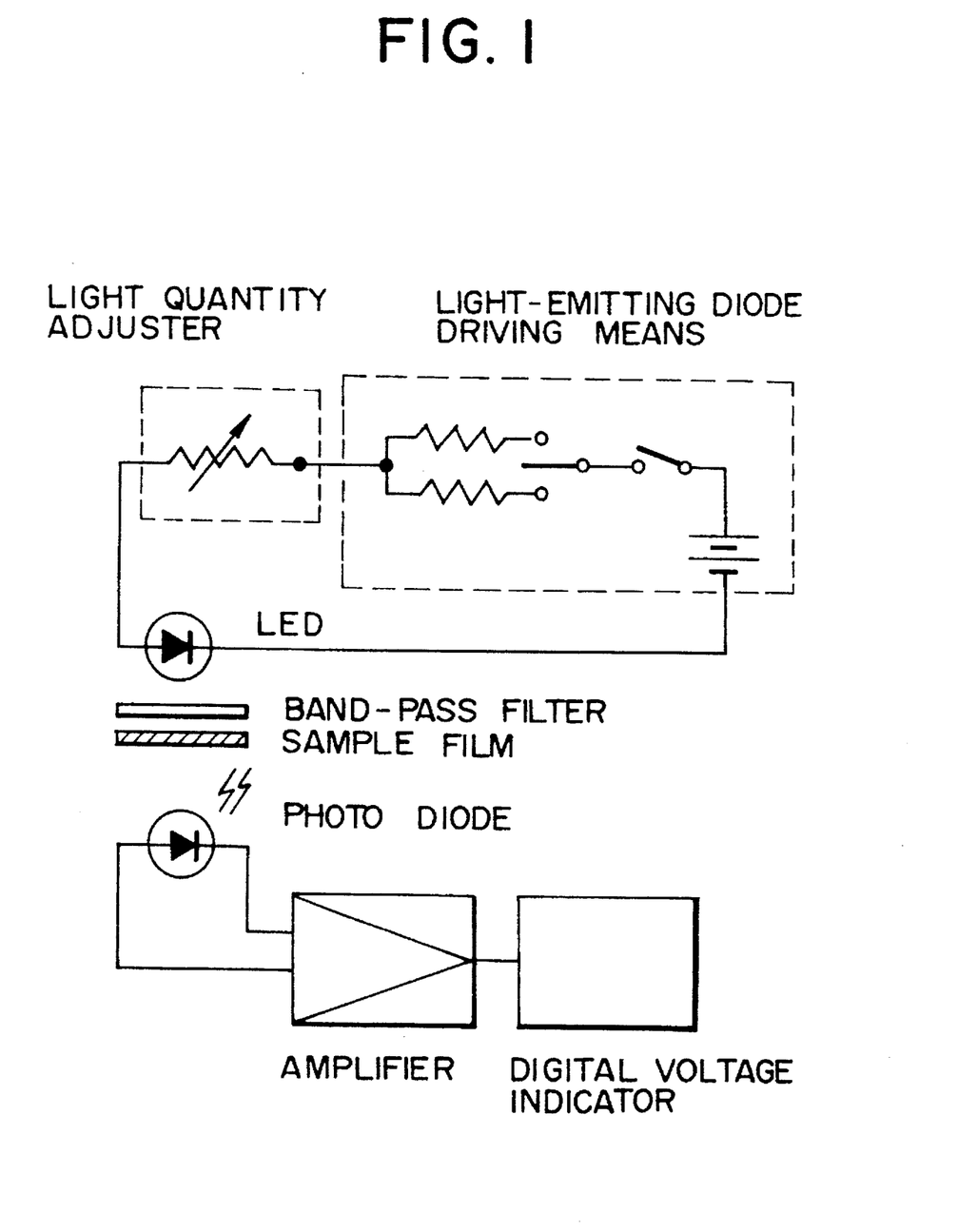
FIG. 1 is a diagram showing the measurement principle in this invention.

The means for allowing the diode to emit a light and adjusting the quantity of light may be any means which is conventionally used for the same purpose such as the electric circuit shown in the light quantity adjuster and the light-emitting diode driving means in FIG. 1.

The pigment used in the coating composition for preparing the band-pass filter may be a Phthalocyanine Blue pigment such as Cyanine Blue #4940N (DAINICHI SEIKA COLOR & CHEMICALS MFG. CO., LTD.), an organic violet pigment such as Hostaperm Violet RLSDICO (Hoechst) or a mixture of the two. The proportion of the pigment in the coating composition is preferably 5–40% by weight.

The binder resin used in the coating composition includes copolymers of ethylenically unsaturated monomers such as styrene, methyl methacrylate, 2-hydroxyethyl methacrylate and acrylic acid.

The coating composition is coated on a resin film such as cellulose triacetate or polyethylene terephthalate or a glass plate in a thickness of several microns.

The photodiode includes those sensitive to lights of 250–800 nm such as BS-112 manufactured by Sharp Corp. and the like.

The means for transferring and digitally indicating electrical signals from the photodiode may be any means which is conventionally used for the same purpose and includes an amplifier and a digital voltage indicator.

Incidentally, the high luminance emission intensity means a standard emission intensity of 1,000 mcd or more.

DESCRIPTION OF PREFERRED EMBODIMENTS

Examples of this invention are explained below referring to FIGS. 1 to 9.

Figure 4:
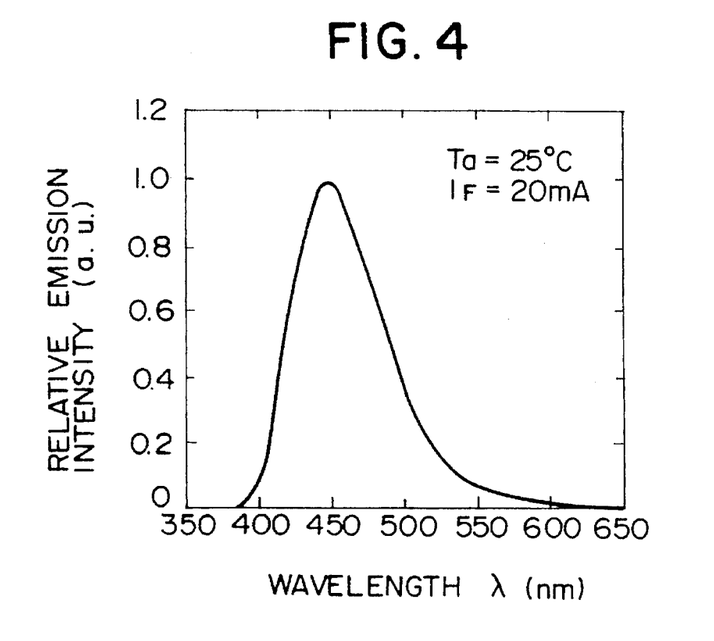
FIG. 4 is a graph showing the characteristics (emission spectrum) of a light-emitting diode in the measurement instrument of this invention.

Light-Emitting Diode NLPB500 manufactured by Nichia Kagaku Kogyo K. K. (peak wavelength: 450 nm; half-value width: 70 nm; orientation characteristics: 15°) was used as a light source, and a group of stationary resistors for changing-over the emitted light intensity range, a rotary switch for selecting the resistor and a variable resistor for adjusting the transmittance to 100% are electrically connected to a 4.5 V direct current source through a lighting switch to prepare a light quantity adjuster. The construction of this light quantity adjuster is shown as an electric circuit in FIG. 1. Also, the emission spectrum of the light-emitting diode in FIG. 1 is as shown in FIG. 4.

As the photodiode in FIG. 1, BS-112 manufactured by Sharp Corp. was used. The amplifier in FIG. 1 was prepared by changing a part of the circuit shown in the "Preparation of Illuminance Meter Using Photodiode" stated in Hisao Nagao, Transistor Technique SPECIAL No. 33, p. 13 (published on May 1, 1992 by CQ Shuppansha). As the digital voltage indicator in FIG. 1, there was used a commercially available digital voltammeter KPS-2324 manufactured by Kaho Musen K.K. which had been partially modified. The measurement instrument was prepared by assembling a direct current source, a main switch, a light-emitting diode lighting switch, a switch for changing-over the quantity of light to be emitted and a variable resistor for adjusting the transmittance to 100%.

The band-pass filter in FIG. 1 was prepared as follows:

A two-liter flask equipped with a thermometer, a dropping funnel, a stirrer and a sample feed opening was charged with 150 parts by weight of toluene and the toluene was warmed to 110° C. Subsequently, a first mixture consisting of 233 parts by weight of styrene, 71 parts by weight of methyl methacrylate, 144 parts by weight of butyl acrylate, 52 parts by weight of 2-hydroxyethyl methacrylate, 2.5 parts by weight of acrylic acid and 5 parts by weight of benzoyl peroxide was dropwise added to the flask over two hours while the mixture was kept at the boiling point. Subsequently, a second mixture consisting of 110 parts by weight of toluene, 75 parts by weight of butyl acetate and 2.5 parts by weight of benzoyl peroxide was dropwise added to the first mixture over two hours after three hours from the start of the dropwise addition of the first mixture, after which the contents of the flask were kept at the boiling point for one hour. Thereafter, 165 parts by weight of xylene was added to dilute the contents, and the contents were cooled. The non-volatile matter thereof was 49.3% (dried at 150° C. for three hours) and the viscosity thereof at 25° C. was 11 poises. A color chip was prepared in the following manner using the resin thus obtained:

Eighty parts by weight of the resin solution, 60 parts by weight of Cyanine Blue #4940N (manufactured by DAIN-ICHISEIKA COLOR & CHEMICALS MFG. CO., LTD. or Hostaperm Violet RLSDICO (manufactured by Hoechst) were well mixed and then sheeted on a twin roll into a sheet while the solvent was allowed to spatter, and then repeatedly sheeted on the roll 100 times in total to prepare a sheet having a pigment content of 60% by weight, and this was ground into fine powder.

The fine powder was dissolved in a solvent mixture of toluene and butyl acetate at a 1/1 volume ratio so that the concentration became 25% by weight, and the solution was then filtered through a 0.5-μ filter and then subjected to centrifugation at 17,000 rpm to remove the undissolved matter, thereby preparing a colored solution.

Figure 5:
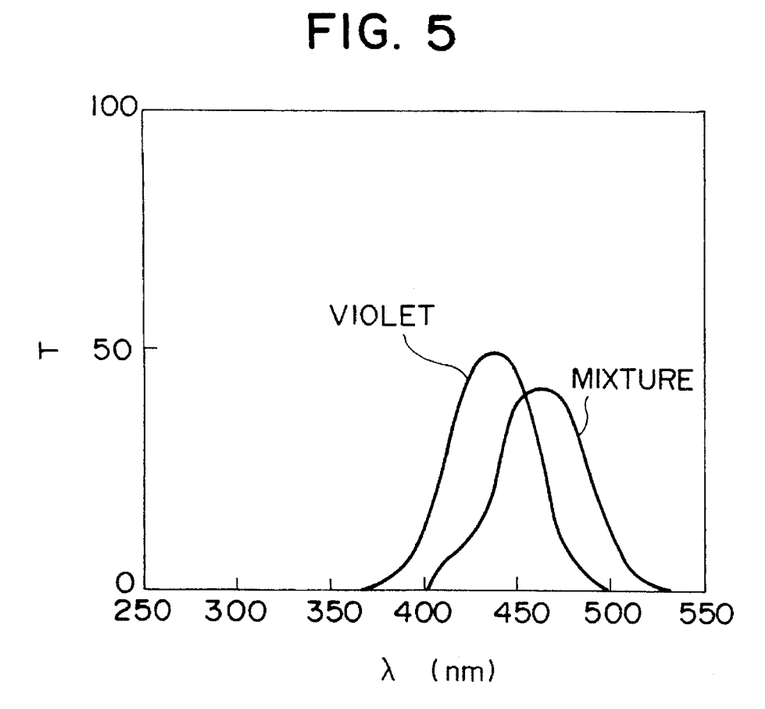
FIG. 5 is a graph showing the characteristics (transmittance) of a band-pass filter (made of polyester) used in the measurement instrument of this invention.
Figure 6:
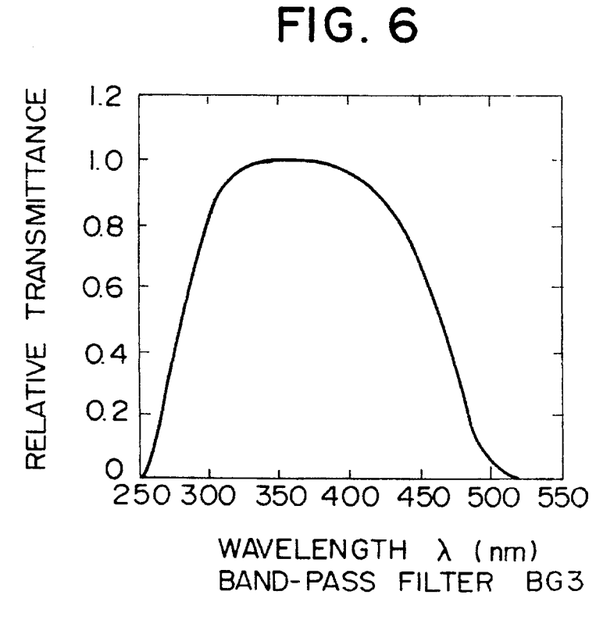
FIG. 6 is a graph showing the characteristics (transmittance of another band-pass filter (made of glass) used in the measurement instrument of this invention.
Figure 7:
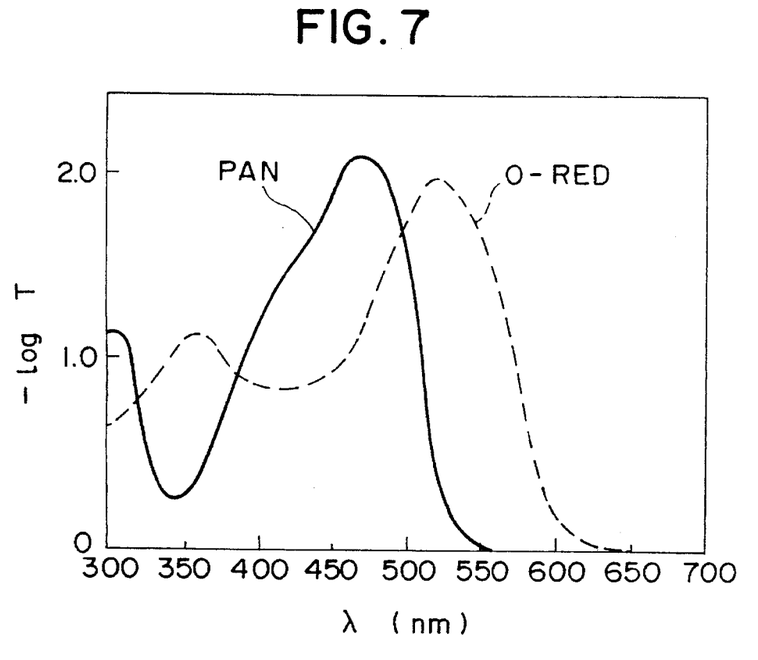
FIG. 7 is a graph showing the characteristics (absorption spectrum) of a dye-impregnated film measured by the measurement instrument of this invention.

A silane coupling agent (Sila Ace S-330 manufactured by Chisso Corp.) was added at a non-volatile matter ratio of about 5% by weight to the colored solution, and 8% by weight of an isocyanate resin (Takenate D-165N (90PX) manufactured by Takeda Chemical Industries, Ltd.) was added, after which, if necessary, the original resin was added. The resulting composition was coated on a polyester film or a glass plate in a thickness of several microns by means of a bar coater, then dried at 120°–150° C. for 10–20 minutes, and thereafter, subjected to measurement of transmittance. By this method, two band-pass filters were prepared using a violet solution alone or a suitable mixed solution of a violet solution and a blue solution. The transmittance characteristics thereof were as shown in FIG. 5. In order to obtain such characteristics, it was necessary to adjust the film thickness and the amount of resin added. Moreover, a commercially available band-pass filter made of glass (GB-3 manufactured by Shot Japan Co., Ltd.) cut to a size of 25 mm×25 mm was used. The transmittance characteristics thereof were as shown in FIG. 6. It was seen that the spectrum of the irradiation light synthesized by FIG. 4 and FIGS. 5 or 6 shows an irradiation light having a peak at about 440–460 nm. Comparing the spectrum of this irradiation light with the spectrum of the dye-impregnated film (see FIG. 7), it can be seen that the spectrum of the irradiation light is present within the range of the skirt of the absorbance curve having a peak at 470 nm of pyridylazo- 2-naphthol (PAN), and in the case of the spectrum of the light-emitting diode alone, the situation that it follows that the quantity of light which does not participate in absorption is measured can be avoided. These filters are all equivalent, and a measurement example using a filter consisting of a violet solution alone is shown below.

The distance between the filter and the end of the light-emitting diode in FIG. 1 was adjusted to 8 mm. Also, the distance between the filter and the light-receiving surface of the photodiode in FIG. 1 was adjusted to 8 mm.

Measurement of absorbance

Figure 2A:
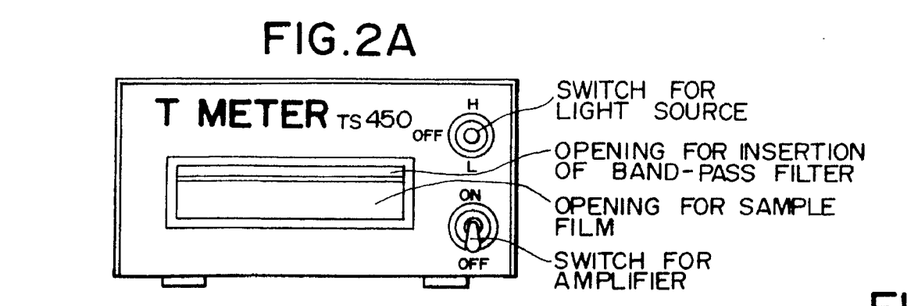
FIG. 2a is a front view of a specific example of the measurement instrument of this invention.
Figures 2B, 2C:
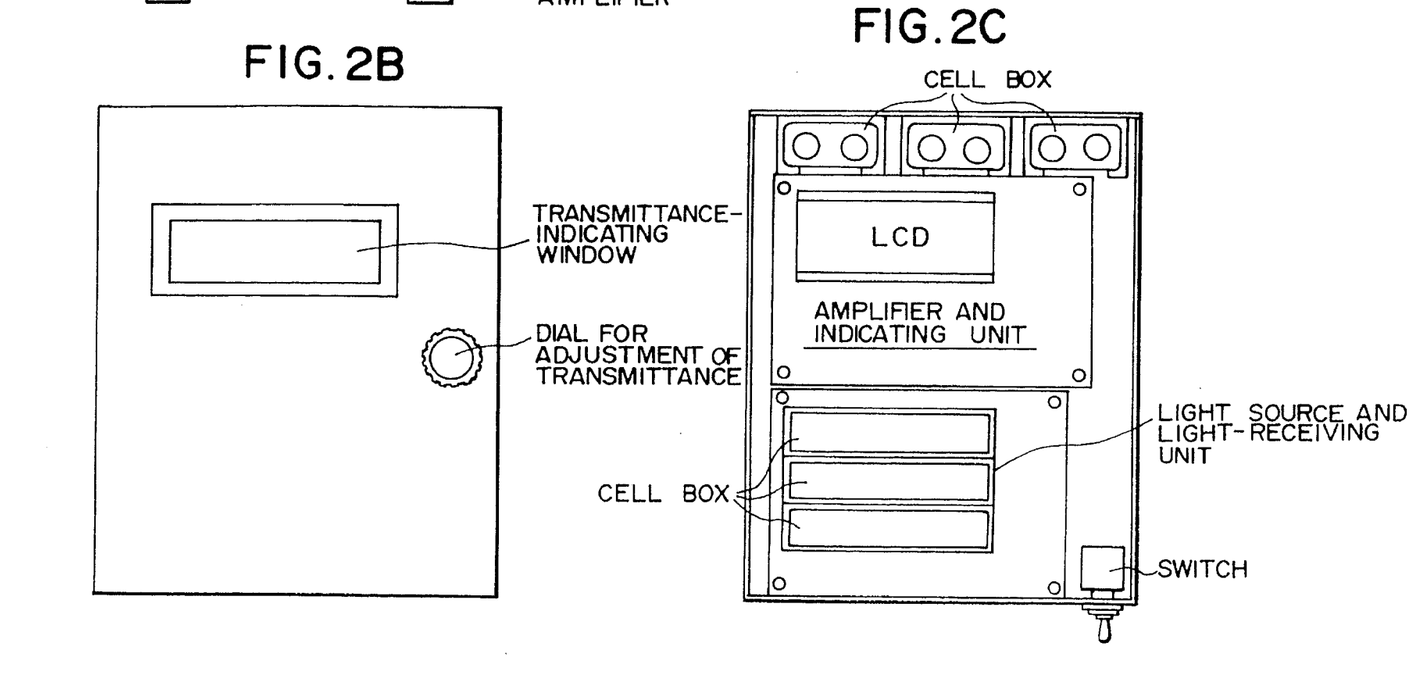
Figure 3:
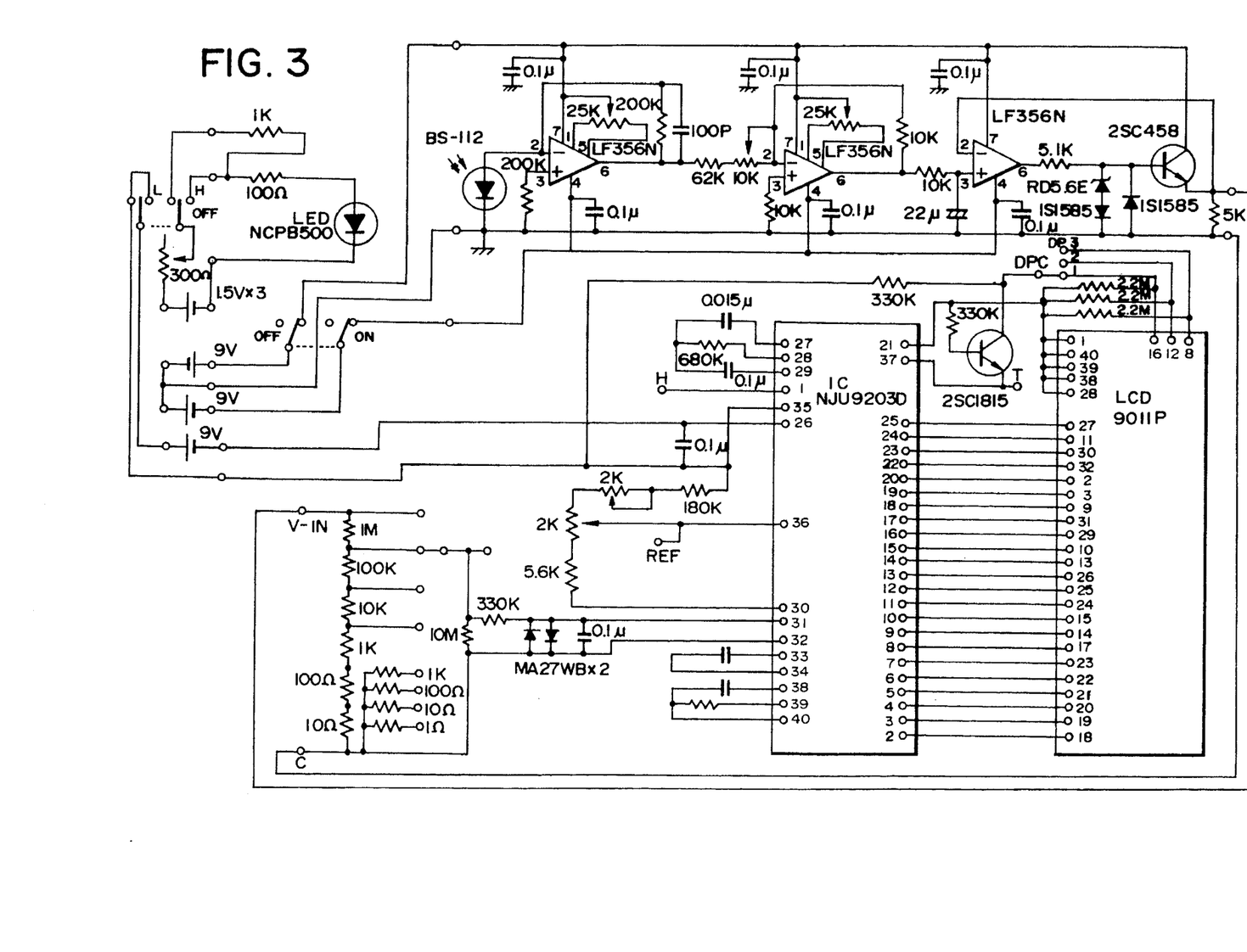

A cellulose triacetate film impregnated with Oil Red or PAN (the dye-impregnated film (sample film) to be measured in FIG. 1) was prepared so that the transmittance at about 470 nm became about 1% when measured by a spectrophotometer (U-3400 manufactured by Hitachi, Ltd.), exposed to light outdoors to fade the dye-impregnated film to prepare a sample, and this sample was subjected to measurement of absorption spectrum by U-3400. The same sample was subjected to measurement of transmittance by the measurement instrument of this invention and the transmittance and an absorbance were obtained. (Transmittance (percentage (100 T), ratio (T)) and absorbance (A) are obtained by the following measurement and determination:

An dye-unimpregnated film is subjected to the measurement instrument of this invention and the irradiation light to which the film is to be exposed is adjusted by the variable registor so that the value shown in the transmittance-indicating window as shown in FIG. 2b becomes 100. Subsequently, a dye-impregnated film is substituted for the dye-unimpregnated film and the value indicated in the transmittance-indicating window is read. This value is a percentage of the above value of 100. The absorbance can be determined by reducing this percentage into a ratio (T) and calculating $-\log T$.)

This absorbance was compared with the former value at 440 nm (the peak wavelength for the measurement instrument of this invention). The results obtained show a straight line as shown in Table 1 and FIG. 8 and are good.

TABLE 1

|     | Oil Red | | | | PAN | | | |
| --- | --- | --- | --- | --- | --- | --- | --- | --- |
|     | U-3400 | | This invention | | U-3400 | | This invention | |
| No. | A | T | A | T | A | T | A | T |
| 1 | 0.935 | 0.116 | 0.798 | 0.159 | 1.745 | 0.033 | 1.455 | 0.035 |
| 2 | 0.78 | 0.166 | 0.665 | 0.216 | 1.600 | 0.025 | 1.318 | 0.0481 |
| 3 | 0.685 | 0.207 | 0.585 | 0.260 | 1.305 | 0.0495 | 1.102 | 0.079 |
| 4 | 0.55 | 0.282 | 0.446 | 0.358 | 0.880 | 0.132 | 0.735 | 0.184 |
| 5 | 0.505 | 0.313 | 0.417 | 0.383 | 0.35 | 0.447 | 0.256 | 0.555 |
| 6 | 0.44 | 0.363 | 0.355 | 0.442 | 0.185 | 0.653 | 0.137 | 0.729 |

Note: Values A (absorbance) are of $-\log T$ ($T = 10^{-A}$).

Figure 8:
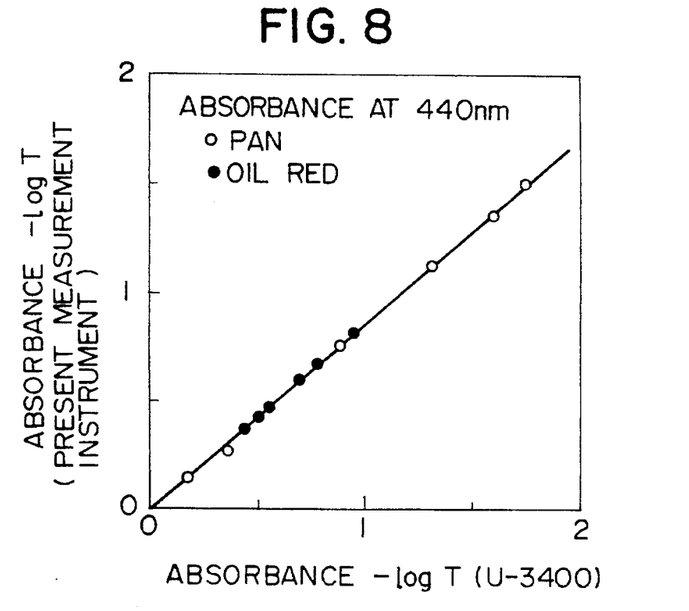
FIG. 8 is a graph for comparing the value of absorbance measured using a wavelength of 440 nm by a spectrophotometer with the value of absorbance measured by the measurement instrument of this invention.

FIG. 8 shows comparisons between the absorbance measured by an exact spectrophotometer using a light of 440 nm and the absorbance measured under the same conditions by the measurement instrument of this invention, and the measurements were conducted using dye-impregnated films having different degrees of color fading.

Figure 9:
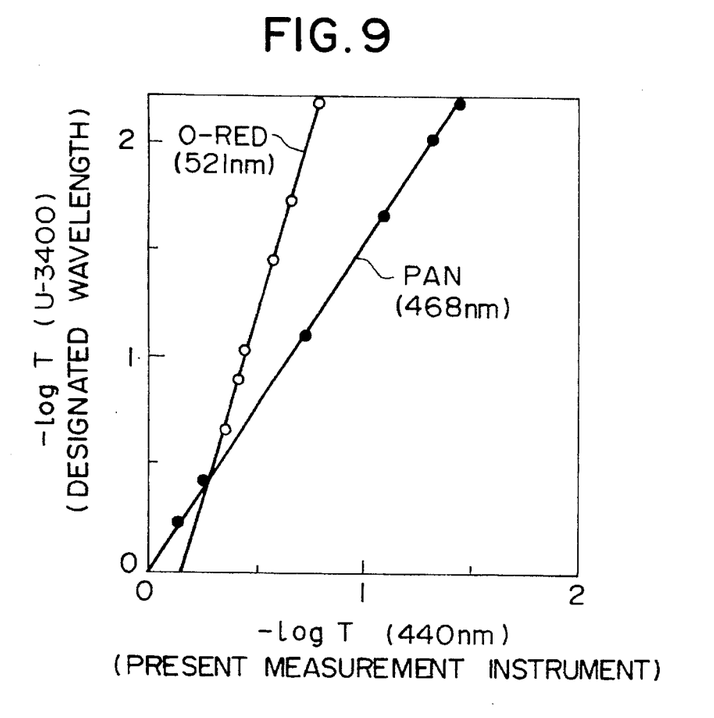
FIG. 9 is calibration curves for determining the exact absorbance value of dye-impregnated film at the absorption peak wavelength to be obtained by a spectrophotometer from the absorbance value obtained using a light having a wavelength of 440 nm by the measurement instrument of this invention.

In addition, the values obtained by the measurement instrument of this invention were compared with those obtained using lights having other wavelength than 440 nm by U-3400 to obtain the calibration line shown in FIG. 9.

That is to say, FIG. 9 is a calibration curve for determining values corresponding to the absorbance values obtained by measurement using lights having wavelengths at the absorption peaks of the respective dyes by an exact spectrophotometer, from the 440 nm absorbance values obtained by subjecting the dye-impregnated films irradiated with a light having a wavelength of 440 nm to measurement by the measurement instrument of this invention.

Using FIG. 9, it becomes possible to determine the absorbance at the peak absorption wavelength of each dye.

From the above data, it is quite clear that the measurement instrument of this invention which is compact and light in weight can be sufficiently put in practice, and the measurement instrument of this invention can contributes greatly to the grasping of causal relation between environment and growth of organisms, and hence, is very useful.

What is claimed is:

1. A simple instrument for measuring the transmittance of a film impregnated with a pyridylazo- 2-naphthol or dimethylphenylazo-2-naphthol dye having a continuous absorption spectrum having a plurality of absorption peaks in the wavelength range of from 350 to 800 nm, which comprises a light-emitting diode having a peak of relative emission intensity in the vicinity of a wavelength of 450 nm; a means for allowing the diode to emit a light and adjusting the quantity of the light; a band-pass filter which consists essentially of a resin film or glass plate coated with a coating composition composed essentially of at least one pigment selected from the group consisting of a Phthalocyanine Blue pigment and an organic violet pigment finely dispersed in a binder resin, and which has a peak of transmittance in the range of from 330 to 480 nm, the transmittance at the peak being 40% or more and the transmittances at 260 nm or less and 520 nm or more being 1% or less, said band-pass filter being placed in such a position that the light emitted by the above light-emitting diode passes directly through the band-pass filter; a photodiode sensitive to the wavelength of the light which has passed through the band-pass filter, said photodiode being placed so as to face the band-pass filter at such a space that a test sample can be inserted into between the band-pass filter and the photodiode and so as to receive the light which has passed through the band-pass filter and the test sample; and a means for transferring the electrical signals from the photodiode and digitally indicating them.

2. The simple instrument according to claim 1, wherein the light-emitting diode is a high luminance-emission intensity light-emitting diode which emits a light having a relative emission intensity peak in the vicinity of a wavelength of 450 nm and a half-value width of 70 nm or less at an emission angle of 20° or less.

3. The simple instrument according to claim 1, wherein the light-emitting diode is NLPB 500 (peak wavelength: 450 nm, the half-value width of 70 nm, orientation characteristics: 15°).

4. The simple instrument according to claim 1, wherein the pigment used in the coating composition is Phthalocyanine Blue.

5. The simple instrument according to claim 1, wherein the resin binder used in the coating composition is a copolymer of styrene, methyl methacrylate, 2-hydroxyethyl methacrylate and acrylic acid.

6. The simple instrument according to claim 1, wherein the photodiode is one sensitive to lights in the range of from 250 nm to 800 nm.

7. A simple instrument for measuring the transmittance of a film impregnated with a pyridylazo-2-naphthol or dimethylphenylazo-2-naphthol dye having a continuous absorption spectrum having a plurality of absorption peaks in the wavelength range of from 350 to 800 nm, which comprises a light source part composed mainly of a high luminance-emission intensity light-emitting diode which emits a light having a relative emission intensity peak in the vicinity of a wavelength of 450 nm and a half-value width of 70 nm or less at an emission angle of 20° or less; a means for allowing the diode to emit a light; a band-pass filter which consists essentially of a resin film or glass plate coated with a coating composition composed essentially of at least one pigment selected from the group consisting a Phthalocyanine Blue pigment and an organic violet pigment finely dispersed in a binder resin, and which has a peak of transmittance in the range of from 330 to 480 nm, the transmittance at the peak being 40% or more and the transmittances at 260 nm or less and 520 nm or more being 1% or less; and a light quantity adjuster composed of a variable resistor and an electric resistance change-over switch capable of adjusting freely the quantity of the irradiation light; and a light-receiving part composed mainly of a photodiode sensitive to the light which has passed through the band-pass filter, an amplifier and a digital voltage indicator.

\* \* \* \* \*